(12) United States Patent
Owen et al.

(10) Patent No.: US 8,058,054 B2
(45) Date of Patent: Nov. 15, 2011

(54) SYSTEMS AND METHODS FOR REAL-TIME PCR

(75) Inventors: Gregory H. Owen, Clarksburg, MD (US); Gregory A. Dale, Gaithersburg, MD (US); Kenton C. Hasson, Gaithersburg, MD (US); Shulin Zeng, Gaithersburg, MD (US); Dwayne W. Warfield, Frederick, MD (US); Sarah Warfield, legal representative, Warfield, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 0 days.

(21) Appl. No.: 11/770,869

(22) Filed: Jun. 29, 2007

(65) Prior Publication Data

US 2008/0176230 A1 Jul. 24, 2008

Related U.S. Application Data

(60) Provisional application No. 60/806,440, filed on Jun. 30, 2006.

(51) Int. Cl.
*C12M 1/00* (2006.01)
*C12P 19/34* (2006.01)

(52) U.S. Cl. .................. 435/283.1; 435/6.12; 435/91.2

(58) Field of Classification Search .................. None
See application file for complete search history.

(56) References Cited

U.S. PATENT DOCUMENTS

| | | | |
|---|---|---|---|
| 4,554,793 A * | 11/1985 | Harding, Jr. .................. 62/126 |
| 5,498,392 A | 3/1996 | Wilding et al. |
| 5,587,128 A | 12/1996 | Wilding et al. |
| 5,641,006 A * | 6/1997 | Autrey et al. .................. 141/94 |
| 5,800,992 A | 9/1998 | Fodor et al. |
| 5,843,727 A | 12/1998 | Hillman et al. |
| 5,872,010 A | 2/1999 | Karger et al. |
| 5,928,907 A | 7/1999 | Woudenberg et al. |
| 5,958,694 A | 9/1999 | Nikiforov |
| 5,993,634 A | 11/1999 | Simpson et al. |
| 6,017,434 A | 1/2000 | Simpson et al. |
| 6,040,138 A | 3/2000 | Lockhart et al. |
| 6,107,044 A | 8/2000 | Nikiforov |
| 6,126,804 A | 10/2000 | Andresen |
| 6,235,471 B1 | 5/2001 | Knapp et al. |
| 6,306,590 B1 | 10/2001 | Mehta et al. |
| 6,309,822 B1 | 10/2001 | Fodor et al. |
| 6,316,201 B1 | 11/2001 | Nikiforov |
| 6,358,387 B1 * | 3/2002 | Kopf-Sill et al. ............. 204/603 |
| 6,391,622 B1 | 5/2002 | Knapp et al. |
| 6,406,893 B1 | 6/2002 | Knapp et al. |
| 6,440,722 B1 | 8/2002 | Knapp et al. |
| 6,444,461 B1 | 9/2002 | Knapp et al. |
| 6,485,625 B1 | 11/2002 | Simpson et al. |
| 6,521,447 B2 | 2/2003 | Zou et al. |
| 6,524,830 B2 | 2/2003 | Kopf-Sill |
| 6,551,784 B2 | 4/2003 | Fodor et al. |

(Continued)

FOREIGN PATENT DOCUMENTS

EP  1418233 A1  5/2004

(Continued)

*Primary Examiner* — Samuel Woolwine

(74) *Attorney, Agent, or Firm* — Rothwell, Figg, Ernst & Manbeck, pc

(57) ABSTRACT

In one aspect, the present invention provides a systems and methods for the real-time amplification and analysis of a sample of DNA.

24 Claims, 14 Drawing Sheets

U.S. PATENT DOCUMENTS

| | | | |
|---|---|---|---|
| 6,551,841 B1 | 4/2003 | Wilding et al. | |
| 6,605,472 B1 | 8/2003 | Skinner et al. | |
| 6,670,133 B2 | 12/2003 | Knapp et al. | |
| 6,670,153 B2 | 12/2003 | Stern | |
| 6,849,411 B2 | 2/2005 | Knapp et al. | |
| 6,911,345 B2 | 6/2005 | Quake et al. | |
| 6,953,676 B1 | 10/2005 | Wilding et al. | |
| 6,960,437 B2 | 11/2005 | Enzelberger et al. | |
| 6,977,163 B1 | 12/2005 | Mehta | |
| 7,105,300 B2 | 9/2006 | Parce et al. | |
| 7,118,910 B2 | 10/2006 | Unger et al. | |
| 7,153,673 B2 | 12/2006 | Stern | |
| 7,156,969 B2 | 1/2007 | Mehta et al. | |
| 7,157,232 B2 | 1/2007 | Miles et al. | |
| 2002/0084510 A1 | 7/2002 | Jun et al. | |
| 2002/0197603 A1 | 12/2002 | Chow et al. | |
| 2002/0197630 A1* | 12/2002 | Knapp et al. | 435/6 |
| 2003/0073229 A1* | 4/2003 | Greenstein et al. | 435/287.2 |
| 2003/0104466 A1 | 6/2003 | Knapp et al. | |
| 2003/0186296 A1 | 10/2003 | Fodor et al. | |
| 2004/0053268 A1* | 3/2004 | Karlsen | 435/6 |
| 2004/0245521 A1* | 12/2004 | Faris | 257/40 |
| 2005/0042639 A1 | 2/2005 | Knapp et al. | |
| 2005/0052646 A1* | 3/2005 | Wohlstadter et al. | 356/311 |
| 2005/0129580 A1* | 6/2005 | Swinehart et al. | 422/100 |
| 2005/0158725 A1 | 7/2005 | Yukimasa et al. | |
| 2005/0202470 A1 | 9/2005 | Sundberg et al. | |
| 2005/0221373 A1 | 10/2005 | Enzelberger et al. | |
| 2005/0244933 A1 | 11/2005 | Panda et al. | |
| 2006/0246493 A1 | 11/2006 | Jensen et al. | |
| 2007/0026421 A1* | 2/2007 | Sundberg et al. | 435/6 |

FOREIGN PATENT DOCUMENTS

WO     WO 9641864 A1 * 12/1996

* cited by examiner

SYSTEMS AND METHODS FOR REAL-TIME PCR

This application claims the benefit of Provisional Patent Application No. 60/806,440, filed on Jun. 30, 2006, which is incorporated herein by this reference.

This application is related to patent application Ser. No. 11/505,358, filed on Aug. 17, 2006, which is incorporated herein by this reference.

BACKGROUND

1. Field of the Invention

The present invention relates to methods for amplifying nucleic acids in micro-channels. In some embodiments, the present invention relates to methods for performing a real-time polymerase chain reaction (PCR) in a continuous-flow microfluidic system and to methods for monitoring real-time PCR in such systems.

2. Discussion of the Background

The detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, may facilitate disease diagnosis and prognosis, marker assisted selection, correct identification of crime scene features, the ability to propagate industrial organisms and many other techniques. Determination of the integrity of a nucleic acid of interest can be relevant to the pathology of an infection or cancer.

One of the most powerful and basic technologies to detect small quantities of nucleic acids is to replicate some or all of a nucleic acid sequence many times, and then analyze the amplification products. PCR is perhaps the most well-known of a number of different amplification techniques.

PCR is a powerful technique for amplifying short sections of DNA. With PCR, one can quickly produce millions of copies of DNA starting from a single template DNA molecule. PCR includes a three phase temperature cycle of denaturation of DNA into single strands, annealing of primers to the denatured strands, and extension of the primers by a thermostable DNA polymerase enzyme. This cycle is repeated so that there are enough copies to be detected and analyzed.

In principle, each cycle of PCR could double the number of copies. In practice, the multiplication achieved after each cycle is always less than 2. Furthermore, as PCR cycling continues, the buildup of amplified DNA products eventually ceases as the concentrations of required reactants diminish.

For general details concerning PCR, see Sambrook and Russell, *Molecular Cloning—A Laboratory Manual* (3rd Ed.), Vols. 1-3, Cold Spring Harbor Laboratory, Cold Spring Harbor, N.Y. (2000); *Current Protocols in Molecular Biology*, F. M. Ausubel et al., eds., Current Protocols, a joint venture between Greene Publishing Associates, Inc. and John Wiley & Sons, Inc., (supplemented through 2005) and *PCR Protocols A Guide to Methods and Applications*, M. A. Innis et al., eds., Academic Press Inc. San Diego, Calif. (1990).

Real-time PCR refers to a growing set of techniques in which one measures the buildup of amplified DNA products as the reaction progresses, typically once per PCR cycle. Monitoring the accumulation of products over time allows one to determine the efficiency of the reaction, as well as to estimate the initial concentration of DNA template molecules. For general details concerning real-time PCR see *Real-Time PCR: An Essential Guide*, K. Edwards et al., eds., Horizon Bioscience, Norwich, U.K. (2004).

Several different real-time detection chemistries now exist to indicate the presence of amplified DNA. Most of these depend upon fluorescence indicators that change properties as a result of the PCR process. Among these detection chemistries are DNA binding dyes (such as SYBR® Green) that increase fluorescence efficiency upon binding to double stranded DNA. Other real-time detection chemistries utilize Foerster resonance energy transfer (FRET), a phenomenon by which the fluorescence efficiency of a dye is strongly dependent on its proximity to another light absorbing moiety or quencher. These dyes and quenchers are typically attached to a DNA sequence-specific probe or primer. Among the FRET-based detection chemistries are hydrolysis probes and conformation probes. Hydrolysis probes (such as the TaqMan® probe) use the polymerase enzyme to cleave a reporter dye molecule from a quencher dye molecule attached to an oligonucleotide probe. Conformation probes (such as molecular beacons) utilize a dye attached to an oligonucleotide, whose fluorescence emission changes upon the conformational change of the oligonucleotide hybridizing to the target DNA.

A number of commercial instruments exist that perform real-time PCR. Examples of available instruments include the Applied Biosystems PRISM 7500, the Bio-Rad iCylcer, and the Roche Diagnostics LightCycler 2.0. The sample containers for these instruments are closed tubes which typically require at least a 10 μl volume of sample solution. If the lowest concentrations of template DNA detectable by a particular assay were on the order of one molecule per microliter, the detection limit for available instruments would be on the order of tens of targets per sample tube. Therefore, in order to achieve single molecule sensitivity, it is desirable to test smaller sample volumes, in the range of 1-1000 nl.

More recently, a number of high throughput approaches to performing PCR and other amplification reactions have been developed, e.g., involving amplification reactions in microfluidic devices, as well as methods for detecting and analyzing amplified nucleic acids in or on the devices. Thermal cycling of the sample for amplification is usually accomplished in one of two methods. In the first method, the sample solution is loaded into the device and the temperature is cycled in time, much like a conventional PCR instrument. In the second method, the sample solution is pumped continuously through spatially varying temperature zones.

For example, Lagally et al. (*Anal Chem* 73:565-570 (2001)) demonstrated amplification and detection of single template DNA in a 280 nl PCR chamber. Detection of products was made post-PCR using capillary electrophoresis. On the other hand, Kopp et al. (*Science* 280:1046-1048 (1998)) demonstrated continuous-flow PCR using a glass substrate with a serpentine channel passing over three constant temperature zones at 95° C. (denature), 72° C. (extension), and 60° C. (annealing). The 72° C. zone was located in the central region and had to be passed through briefly in going from 95° C. to 60° C.

Detection was made post-PCR using gel electrophoresis. Since this PCR technique is not based on heating the entire surfaces of the reaction vessel, the reaction rate is determined by a flow rate, not a heating/cooling rate. Neither of these references described real-time monitoring of the PCR reaction.

Park et al. (*Anal Chem* 75:6029-6033 (2003)) describe a continuous-flow PCR device that uses a polyimide coated fused silica capillary wrapped into a helix around three temperature-controlled blocks. Sample volumes were 2 μl. Detection was made post PCR using gel electrophoresis. Reference was made to the possibility of adapting their instrument for real-time PCR by using a capillary coated with PTFE instead of non-transparent polyimide. See also, Hahn et al. (WO 2005/075683).

Enzelberger et al. (U.S. Pat. No. 6,960,437) describe a microfluidic device that includes a rotary channel having three temperature zones. A number of integrated valves and pumps are used to introduce the sample and to pump it through the zones in a rotary fashion.

Knapp et al. (U.S. Patent Application Publication No. 2005/0042639) describe a microfluidic device capable of single molecule amplification. A planar glass device with several straight parallel channels is disclosed. A mixture of target DNA and PCR reagents is injected into these channels. In a first embodiment, the channels are filled with this mixture and flow is stopped. Then the entire length of the channels is thermally cycled. After thermal cycling is completed, the channels are imaged in order to detect regions of fluorescence where DNA has been amplified. In a second embodiment, the PCR mixture flows continuously through the amplification zone as the temperature is cycled, and fluorescence is detected downstream of the amplification zone. Different degrees of amplification are achieved by altering the time spent in cycling, through changing distance traveled under cycling, and the like. It is worth noting that this method varies conditions (such as cycles experienced) for separate consecutive sample elements, rather than monitoring the progress of individual sample elements over time.

A need exists for robust, high throughput methods of real-time PCR that can be performed efficiently and accurately.

SUMMARY

The present invention relates to systems and methods for amplifying nucleic acids in micro-channels. In some embodiments, the present invention relates to systems and methods for performing a real-time polymerase chain reaction (PCR) in a continuous-flow microfluidic system and to systems and methods for monitoring real-time PCR in such systems.

Thus, in a first aspect, the present invention provides a system for performing real-time PCR and melting of DNA. In some embodiments, the system includes: a microfluidic device comprising: a microfluidic channel having a PCR zone and a DNA melting zone, a first reagent well in fluid communication with the channel and a second reagent well in fluid communication with the channel; a sipper connected to the microfluidic device, the sipper being in fluid communication with the channel; a pump for forcing a sample to flow through the channel; a well plate comprising a buffer well for storing a buffer solution and a sample well for storing a sample solution containing a DNA sample; a buffer solution storage container for storing a buffer solution, the buffer solution storage container being in fluid communication with the buffer well of the well plate; a positioning system operable to position the well plate; a temperature control system for cycling the temperature of a sample while the sample flows through the PCR zone of the channel and for providing heat for melting the DNA contained in the sample while the sample flows through the DNA melting zone; an imaging system for detecting emissions from the PCR zone and from the DNA melting zone, the imaging system comprising: an excitation source and a detector configured and arranged to detect emissions from the PCR zone and/or the DNA melting zone; and a main controller in communication with (a) the temperature control system, (b) the positioner, (c) the imaging system, and (d) a display device.

In a second aspect, the present invention provides a method for performing real-time PCR and melting of DNA. In some embodiments, the method includes: creating a script, wherein the script contains configuration information; preparing a microfluidic device having a microfluidic channel having a PCR zone and a DNA melting zone; reading the script to obtain the configuration information; positioning a well plate relative to the device, the well plate having a buffer well containing a buffer solution and sample well containing a sample solution containing a DNA sample; activating a pump, wherein the pump is configured to create a pressure differential that causes the sample solution to flow through the channel, wherein the sample flows through the PCR zone prior to flowing through the DNA melting zone; while the sample is flowing through the channel: cycling the temperature of the sample according to configuration information included in the script as the sample flows through the PCR zone to amplify the DNA sample; obtaining images of the sample as the sample flows through the PCR zone; processing the images; and melting the amplified DNA.

The above and other embodiments of the present invention are described below with reference to the accompanying drawings.

BRIEF DESCRIPTION OF THE DRAWINGS

The accompanying drawings, which are incorporated herein and form part of the specification, illustrate various embodiments of the present invention. In the drawings, like reference numbers indicate identical or functionally similar elements.

DETAILED DESCRIPTION OF PREFERRED EMBODIMENTS

As used herein, the words "a" and "an" mean "one or more."

Figure 1:
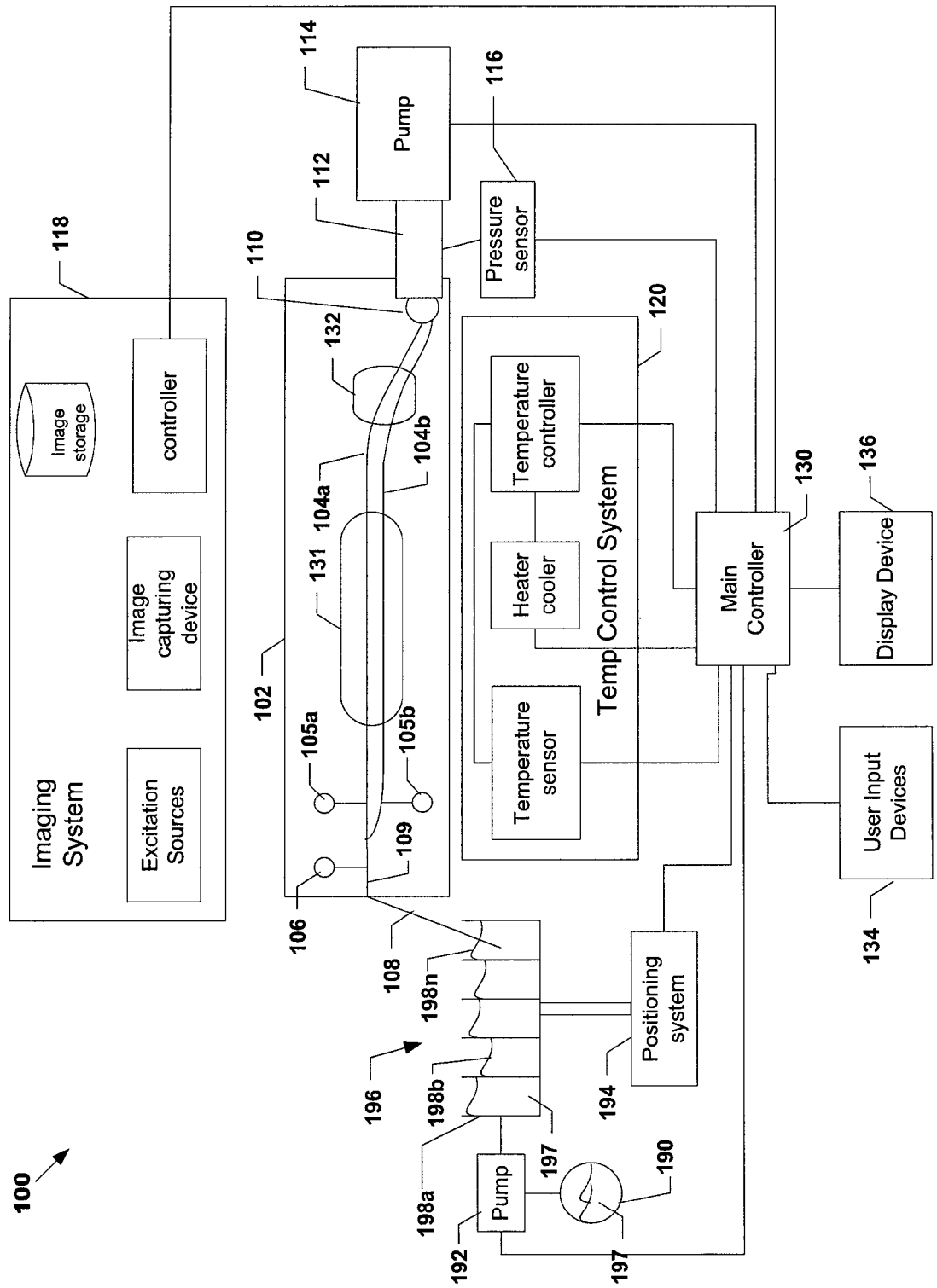
FIG. 1 is a block diagram illustrating a system according to some embodiments of the invention.

The present invention provides systems and methods for real time PCR and high resolution thermal melt. Referring to FIG. 1, FIG. 1 illustrates a functional block diagram of a system 100 according to some embodiments of the invention. As illustrated in FIG. 1, system 100 may include a microfluidic device 102. Microfluidic device 102 may include one or more microfluidic channels 104. In the examples shown, device 102 includes two microfluidic channels, channel 104a and channel 104b. Although only two channels are shown in the exemplary embodiment, it is contemplated that device 102 may have fewer than two or more than two channels. For example, in some embodiments, device 102 includes eight channels 104.

Device 102 may include two DNA processing zones, a DNA amplification zone 131 (a.k.a., PCR zone 131) and a DNA melting zone 132. A DNA sample traveling through the PCR zone 131 may undergo PCR, and a DNA sample passing through melt zone 132 may undergo high resolution thermal melting. As illustrated in FIG. 1, PCR zone 131 includes a first portion of channels 104 and melt zone 132 includes a second portion of channels 104, which is down stream from the first portion.

Device 102 may also include a sipper 108. Sipper 108 may be in the form of a hollow tube. Sipper 108 has a proximal end that is connected to an inlet 109 which inlet couples the proximal end of sipper 108 to channels 104.

Device 102 may also include a common reagent well 106, which is connected to inlet 109. Device 102 may also include a locus specific reagent well 105 for each channel 104. For example, in the embodiment shown, device 102 includes a locus specific reagent well 105a, which is connected to channel 104a, and may include a locus specific reagent well 105b which is connected to channel 104b. Device 102 may also include a waste well 110 for each channel 104.

The solution that is stored in the common reagent well 106 may contain dNTPs, polymerase enzymes, salts, buffers, surface-passivating reagents, one or more non-specific fluorescent DNA detecting molecules, a fluid marker and the like. The solution that is stored in a locus specific reagent well 105 may contain PCR primers, a sequence-specific fluorescent DNA probe or marker, salts, buffers, surface-passivating reagents and the like.

In order to introduce a sample solution into the channels 104, system 100 may include a well plate 196 that includes a plurality of wells 198, at least some of which contain a sample solution (e.g., a solution containing a nucleic acid sample). In the embodiment shown, well plate 196 is connected to a positioning system 194 which is connected to a main controller 130.

Main controller 130 may be implemented using a PXI-8105 controller which is available from National Instruments Corporation of Austin, Tex. Positioning system 194 may include a positioner (e.g., the MX80 positioner available from Parker Hannifin Corporation of PA ("Parker")) for positioning well plate 196, a stepping drive (e.g., the E-AC Microstepping Drive available from Parker) for driving the positioner, and a controller (e.g., the 6K4 controller available from Parker) for controlling the stepping drive.

To introduce a sample solution into the channels 104, the positioning system 194 is controlled to move well plate 196 such that the distal end of sipper 108 is submerged in the sample solution stored in one of the wells 198. FIG. 1 shows the distal end of 108 being submerged within the sample solution stored in well 198n.

In order to force the sample solution to move up the sipper and into the channels 104, a vacuum manifold 112 and pump 114 may be employed. The vacuum manifold 112 may be operably connected to a portion of device 102 and pump 114 may be operably connected to manifold 112. When pump 114 is activated, pump 114 creates a pressure differential (e.g., pump 114 may draw air out of a waste well 110), and this pressure differential causes the sample solution stored in well 198n to flow up sipper 108 and through inlet channel 109 into channels 104. Additionally, this causes the reagents in wells 106 and 105 to flow into a channel. Accordingly, pump 114 functions to force a sample solution and real-time PCR reagents to flow through channels 104. As illustrated in FIG. 1, melt zone 132 is located downstream from PCR zone 131. Thus, a sample solution will flow first through the PCR zone and then through the melting zone.

Referring back to well plate 196, well plate 196 may include a buffer solution well 198a. In one embodiment, buffer solution well 198a holds a buffer solution 197. Buffer solution 197 may comprise a conventional PCR buffer, such as a conventional real-time (RT) PCR buffer. Conventional PCR buffers are available from a number of suppliers, including: Bio-Rad Laboratories, Inc., Applied Biosystems, Roche Diagnostics, and others.

In order to replenish buffer solution well 198a with the buffer solution 197, system 100 may include a buffer solution storage container 190 and a pump 192 for pumping the buffer solution 197 from container 190 into well 198a. Additionally, pump 192 may be configured to not only add solution 197 to well 198a, but also remove solution 197 from well 198a, thereby re-circulating the solution 197.

In order to achieve PCR for a DNA sample flowing through the PCR zone 131, the temperature of the sample must be cycled, as is well known in the art. Accordingly, in some embodiments, system 100 includes a temperature control system 120. The temperature control system 120 may include a temperature sensor, a heater/cooler, and a temperature controller. In some embodiments, a temperature control system 120 is interfaced with main controller 130 so that main controller 130 can control the temperature of the samples flowing through the PCR zone and the melting zone.

Main controller 130 may be connected to a display device for displaying a graphical user interface. Main controller 130 may also be connected to user input devices 134, which allow a user to input data and commands into main controller 130.

To monitor the PCR process and the melting process that occur in PCR zone 131 and melt zone 132, respectively, system 100 may include an imaging system 118. Imaging system 118 may include an excitation source, an image capturing device, a controller, and an image storage unit.

Figure 2:
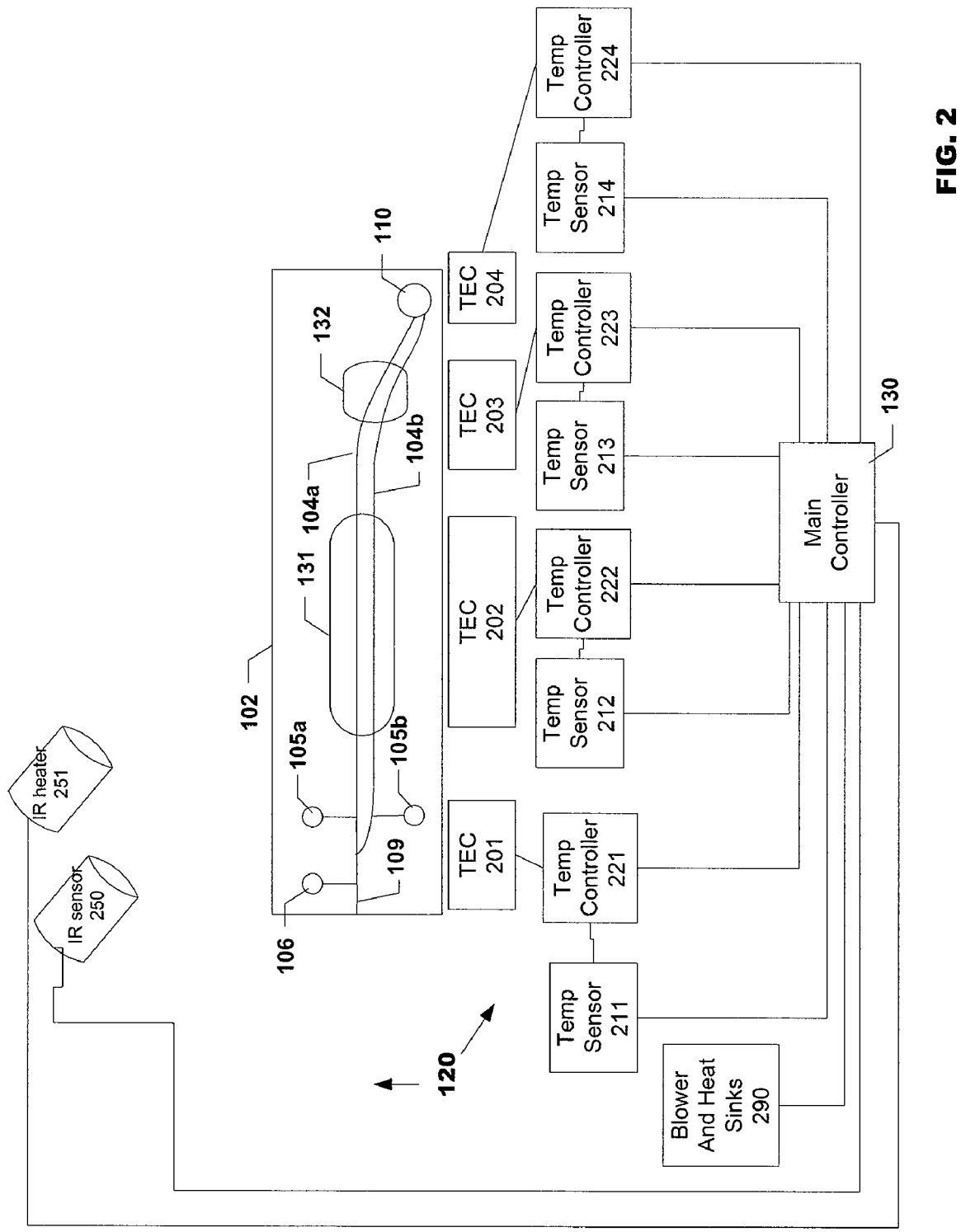
FIG. 2 is a block diagram illustrating a temperature control system according to some embodiments of the invention.

Referring now to FIG. 2, FIG. 2 illustrates the temperature control system 120 according to some embodiments of the invention. As illustrated in FIG. 2, temperature control system 120 may include a number of heating and/or cooling devices (e.g., a thermoelectric cooler (TEC), which is also known as a Peltier device, or other heating/cooling device), a number of temperature controllers, and a number of temperature sensors.

In the embodiment shown, temperature control system 120 includes a TEC 201 for heating and cooling inlet 109, a TEC 202 for heating and cooling the PCR zone, a TEC 203 for heating and cooling the melting zone, and a TEC 204 for heating and cooling the waste well 110. Each TEC 201-204 may be connected to a temperature controller.

For example, in the embodiment shown, TEC 201 is connected to temperature controller 221, TEC 202 is connected to temperature controller 222, TEC 203 is connected to temperature controller 223, and TEC 204 is connected to temperature controller 224. In some embodiments, the temperature controllers 221-224 may be implemented using the Model 3040 Temperature Controller, which is available from Newport Corporation of Irvine, Calif. In other embodiments, controllers 221-224 may consist simply of a power amplifier.

The temperature controllers 221-224 may be interfaced with main controller 130. This will enable main controller 130 to control the temperature of the different regions of device 102. Temperature control system 120 may also include a temperature sensor 211 for monitoring the temperature of inlet 109, a temperature sensor 212 for monitoring the temperature of the PCR zone 131, a temperature sensor 213 for monitoring the temperature of a melting zone 132, and a temperature sensor 214 for monitoring the temperature of the waste well 110. Temperature sensors 211-214 may be in communication with a temperature controller and/or main controller 130, as is illustrated in FIG. 2.

Temperature control system 120 may further include an infrared sensor 250 for monitoring the temperature of the PCR zone 131 and a source of electromagnetic radiation 251 (e.g., a source of infrared, RF, Microwave, etc. radiation) for heating the PCR zone 131. Lastly, temperature control system 120 may include blower and heat sinks 290 for cooling one or more of TEC 201-204.

Figure 3:
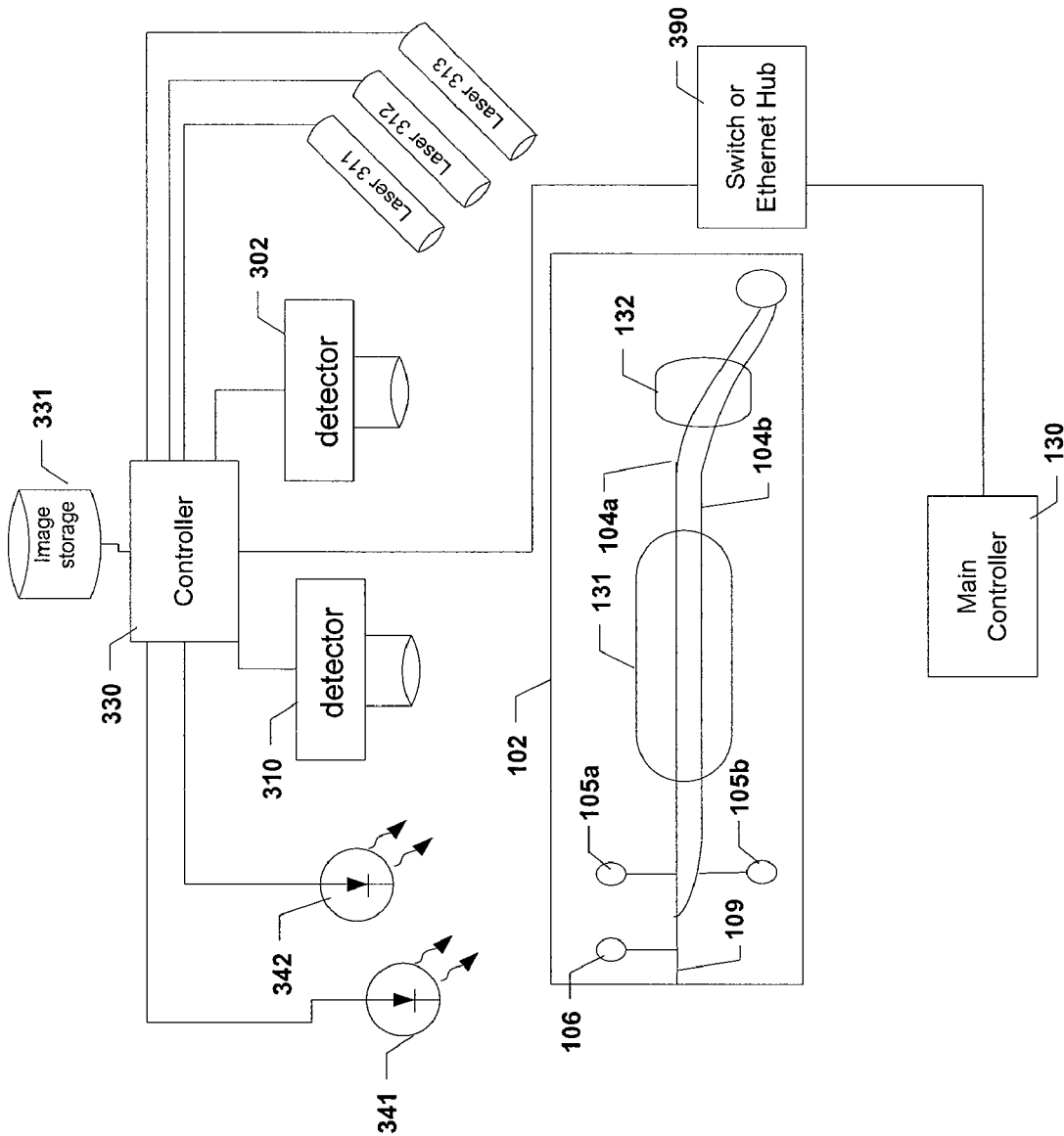
FIG. 3 is a block diagram illustrating an imaging system according to some embodiments of the invention.

Referring now to FIG. 3, FIG. 3 illustrates imaging system 118 according to some embodiments of the invention. As illustrated in FIG. 3, imaging system 118 may include a first detector 310, a second detector 302, a blue LED 341, a red LED 342, a first laser 311, a second laser 312, and a third laser 313. Although two detectors are shown, it is contemplated that imaging system 118 may employ only a single detector.

Detector 310 may be configured and arranged to detect emissions (e.g., fluorescent emissions) from PCR zone 131 and to output image data corresponding to the detected emissions. Detector 310 may be implemented using a conventional digital camera, such as the Canon 5D digital SLR camera. Blue LED 341 and red LED 342 are configured and arranged such that when they are activated they will illuminate the PCR zone 131.

Detector 302 may be configured and arranged to detect emissions from the melting zone 132 and to output image data corresponding to the detected emissions. Detector 302 may be implemented using a digital video camera. In one embodiment, detector 302 is implemented using an electron multiplying charge coupled device (EMCCD).

Lasers 311-313 are configured and arranged to illuminate the melting zone. Each laser may output a different wave length of light. For example, laser 311 may output light having a wave length of 488 nanometers, laser 312 may output light having a wave length of 445 nanometers, and laser 313 may output light having a wave length of 625 nanometers.

Imaging system 118 may include a controller 330 for controlling detector 310, 302 and excitation sources 341, 342, 311, 312 and 313. Controller 330 may also be configured to process image data produced by the detectors. Controller 330 may be implemented using a conventional microprocessor (e.g., controller 330 may consist of a conventional personal computer). Coupled to controller 330 may be an image storage device 331 for storing image data collected by detectors 310 and 302. Controller 330 may be in communication with main controller 130. Controller 330 may be directly connected to main controller or may be connected to main controller through a switch 390 or other communication device (e.g., an Ethernet hub).

Figure 4:
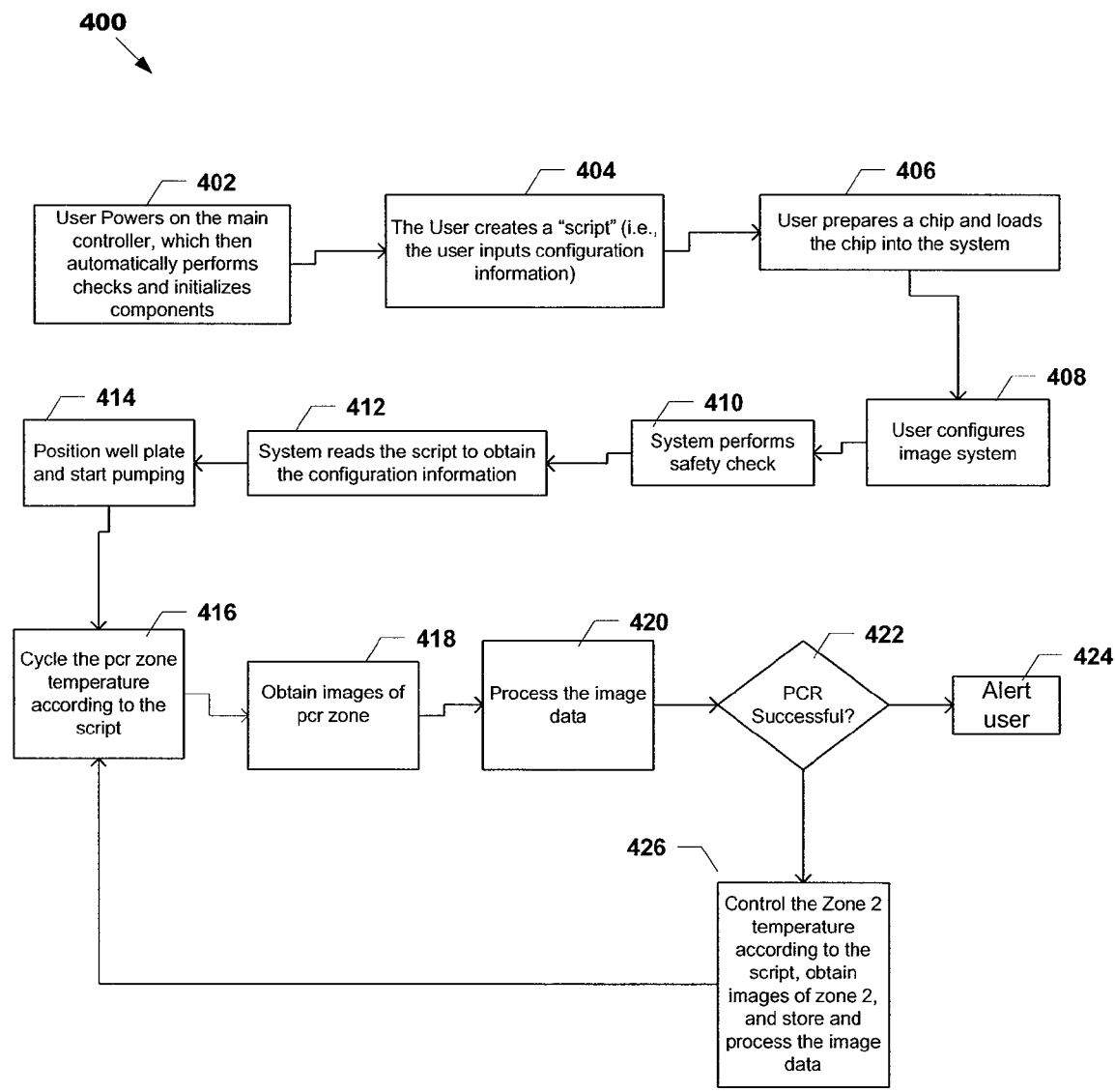
FIG. 4 is a flow chart illustrating a process according to some embodiments of the invention.

Referring now to FIG. 4, FIG. 4 is a flow chart illustrating a process 400 for amplifying and melting DNA according to some embodiments of the invention. Process 400 may begin at 402, where a user turns on main controller 130, which then automatically performs system checks and initializes other components of system 100.

In step 404, the user may create a "script" (i.e., the user may input configuration information). In step 406, the user prepares device 102 and places device 102 into system 100. In step 408, the user may configure and/or adjust imaging system 118. In step 410, main controller 130 may perform safety checks. In step 412, main controller 130 reads the script created by the user to obtain the configuration information.

In step 414, the positioning system 194 positions well plate 196 so that the distal end of sipper 108 is submerged in a sample solution contained within one of the wells 198 of plate 196 and main controller 130 sends a signal to sample pump 114 to begin pumping. The activation of the sample pump 114 causes the sample solution to flow through channels 104. In step 416, while the sample solution is flowing through channels 104, the temperature of the PCR zone 131 is cycled according to the configuration information in the script created by the user.

In step 418, while the temperature of the PCR zone 131 is being cycled, the imaging system 118 obtains images of the PCR zone. In step 420, the image data is processed to determine whether the DNA amplification was successful. In step 422, a decision is made as to whether the PCR was successful. If it was not successful, then the process may proceed to step 424, where the user is alerted. If the PCR was successful then the process may proceed to step 426, where the melting zone 132 temperature is controlled according to the script and, while the temperature is being controlled according to the script, images are obtained and stored. After step 426, the process may proceed back to step 416.

As FIG. 4 demonstrates, a user may use system 100 to amplify a sample of DNA, monitor the amplification process, melt the amplified DNA, and monitor the melting process. Thus, system 100 may provide a valuable tool for DNA analysis.

Figure 5:
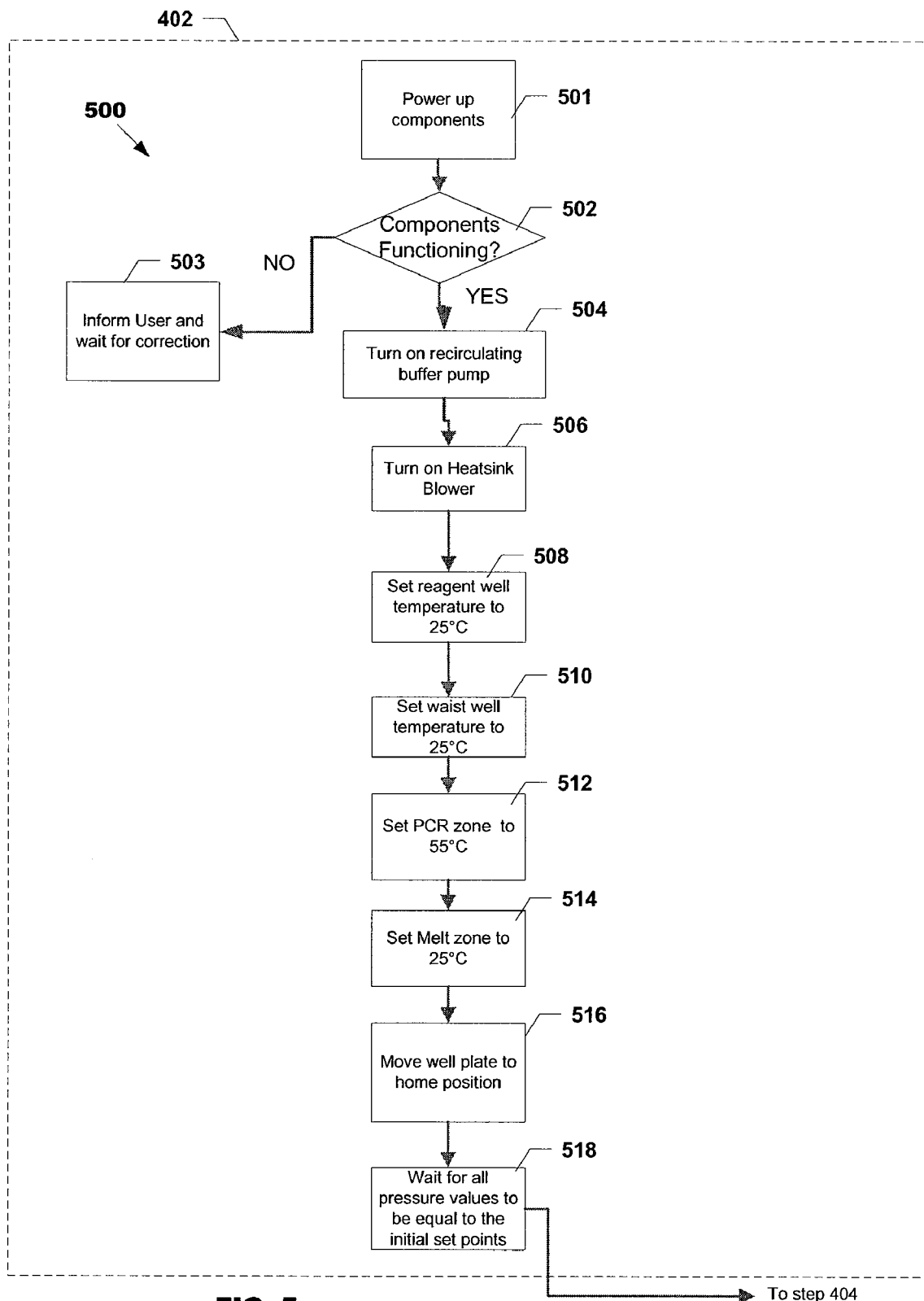
FIG. 5 is a flow chart illustrating a process according to some embodiments of the invention.

Referring now to FIG. 5, FIG. 5 is a flow chart illustrating a process 500, according to some embodiments of the invention, for implementing step 402 of process 400.

Process 500 may begin in step 501 where main controller 130 powers up other components of system 100. In step 502, main controller 130 may determine whether the other components are functioning appropriately. If it is determined that one or more other components are not functioning appropriately, the process may proceed to step 503, where main controller 130 informs the user that there may be a problem. Otherwise, the process may proceed to step 504.

In step 504 main controller 130 activates the upper pump 192. This causes the buffer fluid 197 to fill well 198a. In step 506 main controller 130 activates heat sink and blower 290. In step 508, temperature control system 120 is operated to set the reagent well temperature to 25° C. In step 510, the temperature control system is operated to set the waste well temperature to 25°. In step 512, the temperature control system is operated to set the PCR zone 131 to 55° C. In step 514, the temperature control system is operated to set the melting zone 132 to 25° C. In step 516, the positioning system 194 is used to move the well plate 196 to a home position. In step 518, main controller 130 waits for all pressure values to be equaled to their initial set points.

Figure 6:
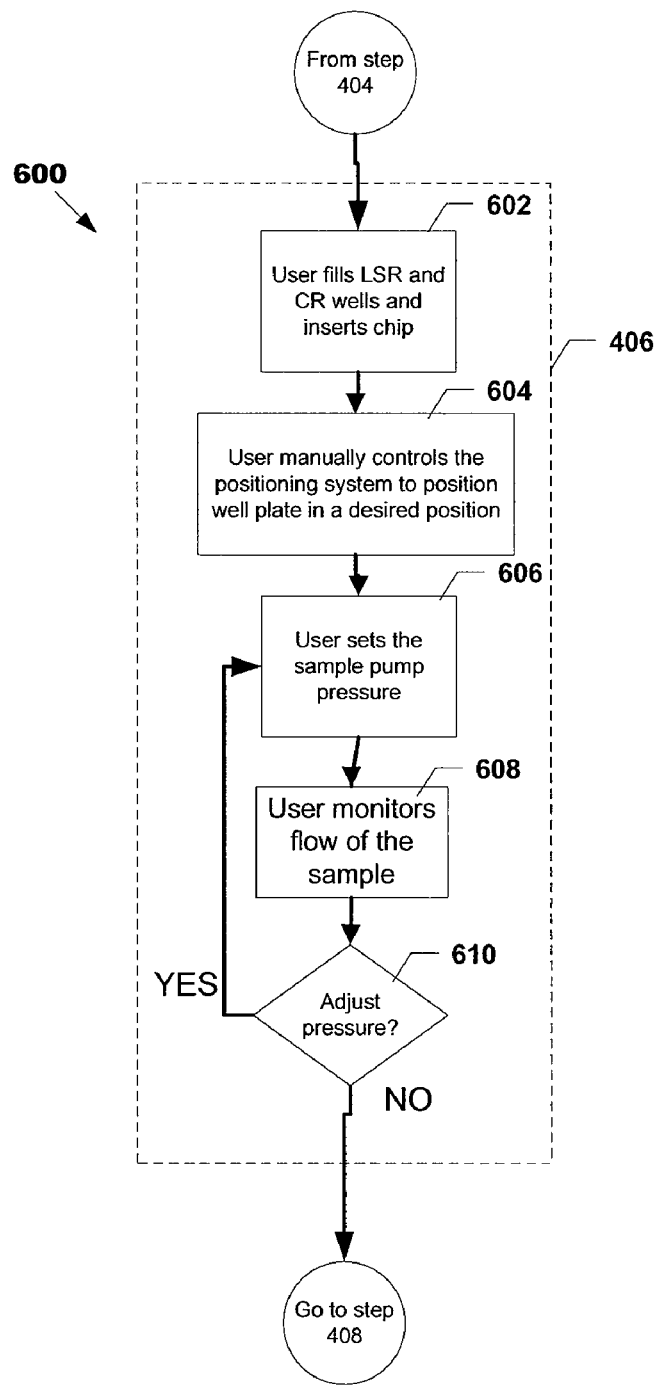
FIG. 6 is a flow chart illustrating a process according to some embodiments of the invention.

Referring now to FIG. 6, FIG. 6 is a flow chart illustrating a process 600, according to some embodiments, for implementing step 406 of process 400.

Process 600 may begin in step 602, where the user fills the locus specific reagent wells 105 and fills the common reagent well 106 and then places the device in a device holder (not shown). In step 604 the user may manually control the positioning system 194 to position the well plate 196 in a desired location. For example, the user may position well plate 196 so that the sipper 108 is located within a desired well 198 of the well plate 196.

In step 606, the user may input a desired channel pressure and may activate the sample pump 114. Activating the sample pump 114 causes the sample solution that is in the well 198 in which sipper 108 is located to enter and flow through channels 104. It also causes the reagent solutions that are in wells 106 and 105 to enter a channel. In step 608, the user may monitor the flow of the sample solution through channels 104. For example, images taken by imaging system 118 will be displayed on display device 136 and the images may show the sample solution moving through the channels 104.

In step 610 the user may decide whether or not to adjust the channel pressure. Adjusting the pressure of the channel will either increase or decrease the rate at which the sample solution flows through the channel. After adjusting the pressure, the sample pump 114 will either pump more or less, depending on whether the user adjusted the pressure up or down.

Figure 7:
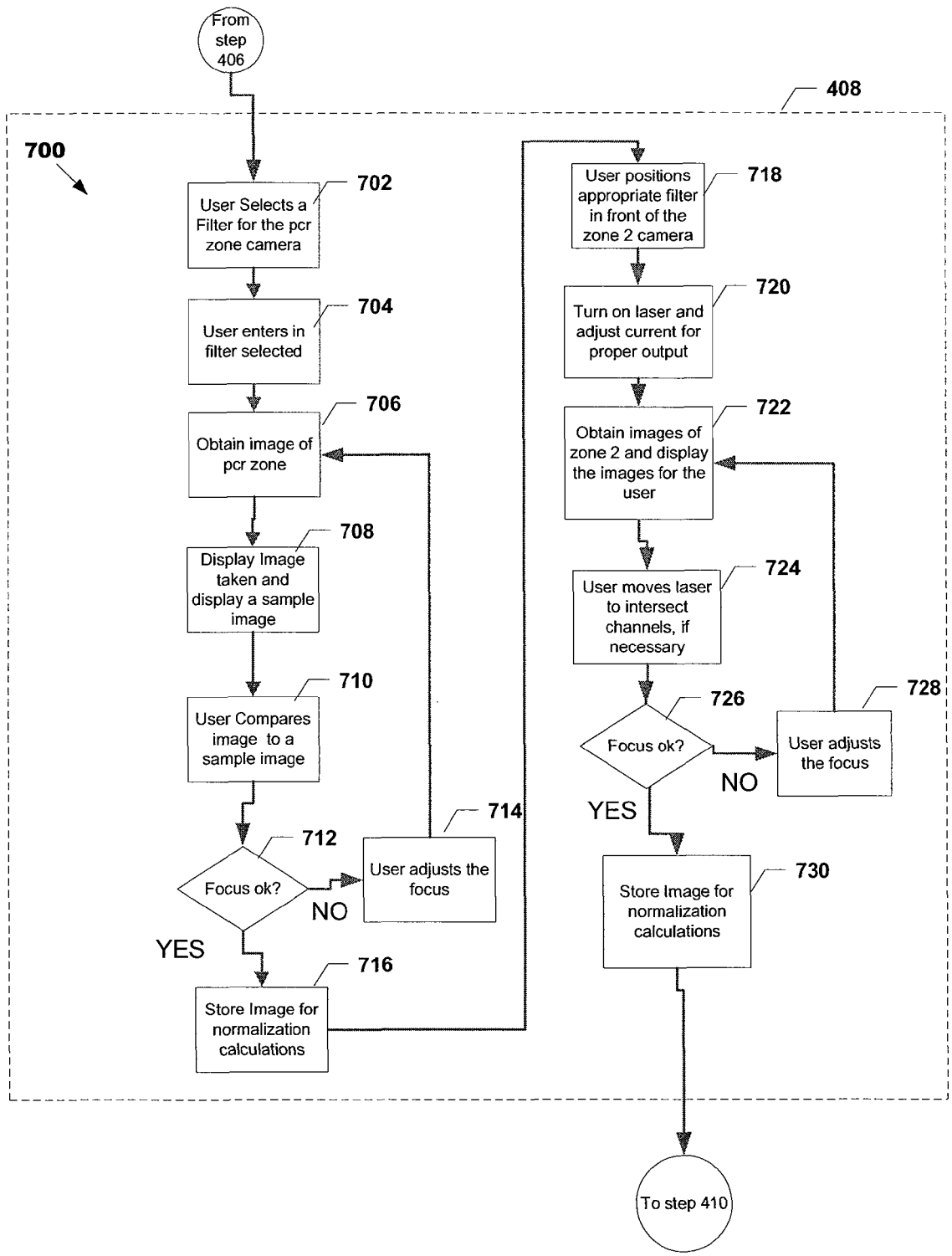
FIG. 7 is a flow chart illustrating a process according to some embodiments of the invention.

Referring now to FIG. 7, FIG. 7 is a flow chart illustrating a process 700, according to some embodiments, for implementing step 408 of process 400.

Process 700 may begin in step 702, where the user may select a filter for detector 310, which is the detector that images the PCR zone 131. In step 704, the user inputs into main controller 130 an identifier identifying the selected filter. In step 706, detector 310 may obtain an image of the PCR zone 131. In step 708, the image may be displayed on the display device 136. Along with displaying the image obtained in 706, main controller 130 may also display on the display device 136a reference image.

In step 710, the user may compare the image obtained in step 706 with the reference image displayed in step 708. If the comparison indicates that the focus of detector 310 is not adjusted properly, then process 700 may proceed to step 714, otherwise it may proceed to step 716. In step 714, the user may adjust the focus of detector 310. For example, the user may move detector 310 either closer to or further away from the PCR zone 131. After step 714, process 700 may go back to step 706. In step 716, the image obtained in step 706 may be stored and used for normalization calculations.

In step 718, the user may position a selected filter in front of detector 302, which is the detector that images the melting zone 132. In step 720, the user may turn on a selected one of the lasers 311-313 and may adjust the output of the selected laser. In step 722, images on the melting zone 132 are obtained and displayed on the display device 136. In step 724, user may adjust the laser to intersect channels 104, if necessary. For example, if the images obtained in step 722 indicate that the laser is not properly aligned, and the user may appropriately align the laser so that it intersects channels 104.

In step 726, user may determine whether the focus of detector 302 is accurate. If the focus is inadequate, process 700 may proceed to step 728, otherwise it may proceed to step 730. In step 728, the user adjusts the focus of detector 302. After step 728, the process may proceed back to step 722. In step 730, the images obtained in step 722 are stored for later normalization calculations.

Figure 8:
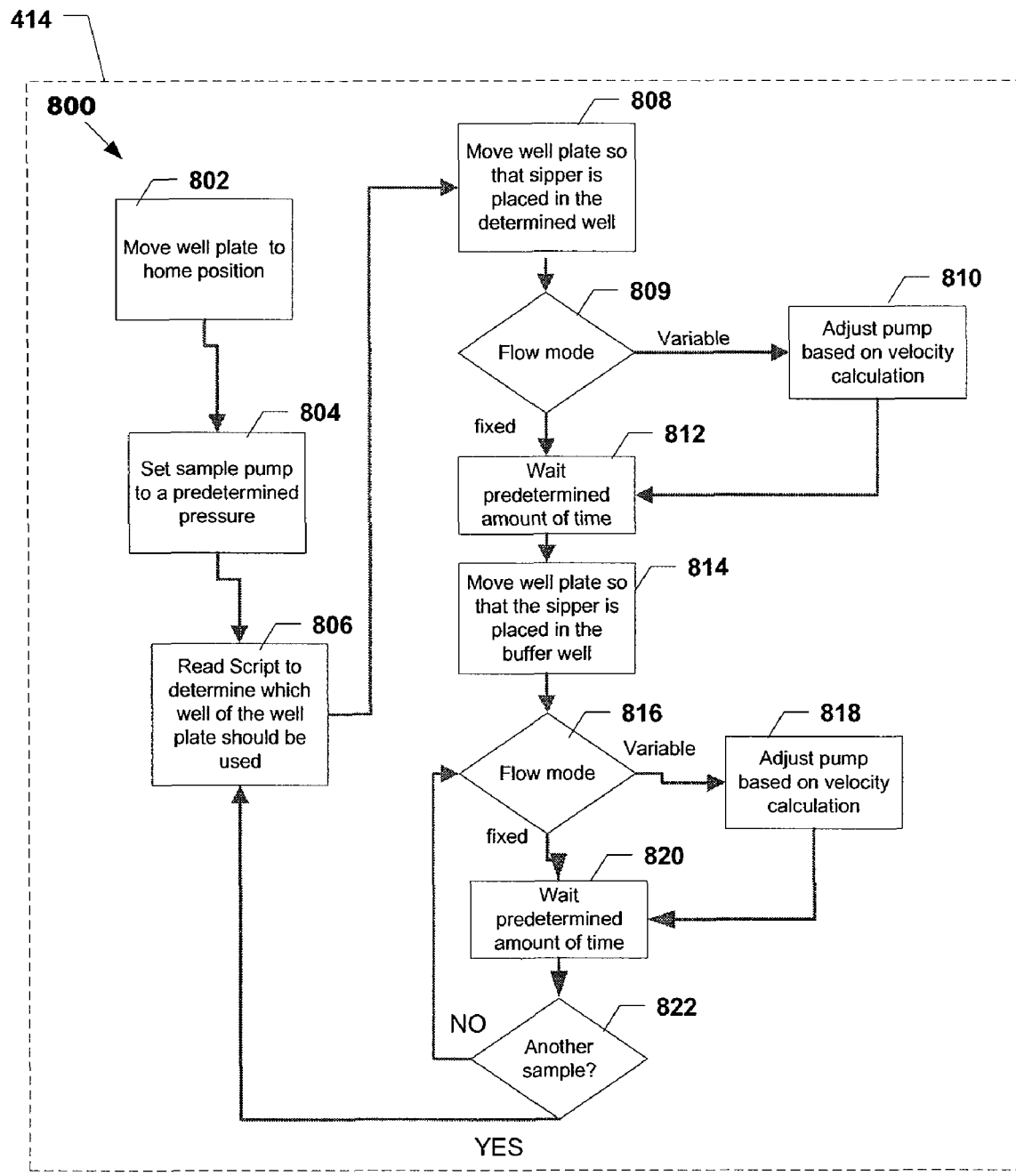
FIG. 8 is a flow chart illustrating a process according to some embodiments of the invention.

Referring now to FIG. 8, FIG. 8 is a flow chart illustrating a process 800, according to some embodiments, for implementing step 414 of process 400.

Process 800 may begin in step 802, where main controller 130 moves well plate 186 to a predetermined "home" position. In step 804, main controller 130 sets the sample pump 114 to a predetermined pressure. In step 806, main controller 130 reads a script created by the user to determine which well of the well plate should be used first. In step 808, main controller 130 causes the positioning system 194 to move the well plate 196 so that a sipper 108 is placed in the well determined in step 806. In step 809 main controller 130 may determine whether the flow mode has been set to a variable flow mode or to a fixed flow mode. If the flow mode has been set to be a variable flow mode then process 800 may proceed to step 810, otherwise it may proceed to step 812.

In step 810, main controller 130 adjusts sample pump 114 based at least in part on a calculation of the velocity of the sample moving through channels 104. This velocity calculation may be based on, among other things, images taken of the sample at different times as the sample moves through the channels 104, such as, for example, as disclosed in U.S. patent application Ser. No. 11/505,358, incorporated herein by reference. In step 812, main controller 130 waits for a predetermined amount of time. This predetermined amount of time may have been set in the script created by the user. Immediately after the predetermined amount of time has expired, process 800 may proceed from step 812 to step 814. In step 814, main controller 130 causes the positioning system 194 to move well plate 196 so that the sipper 108 is placed in the buffer well 198a.

In step 816 main controller 130 determines whether the flow mode has been set to a variable flow mode or to a fixed flow mode. If the flow mode has been set to be a variable flow mode then process 800 may proceed from step 816 to step 818, otherwise process 800 may proceed from step 816 to step 820. In step 818, main controller 130 adjusts the sample pump 114 based, at least in part, on a calculation of the velocity of the sample moving through channel 104. In step 820, main controller 130 waits a predetermined amount of time. In step 822, main controller 130 determines whether another sample should be introduced into the channels 104. If no other sample needs to be introduced into the channels 104, then the process may proceed from step 822 to step 816, otherwise the process may proceed from step 822 to step 806.

Figure 9:
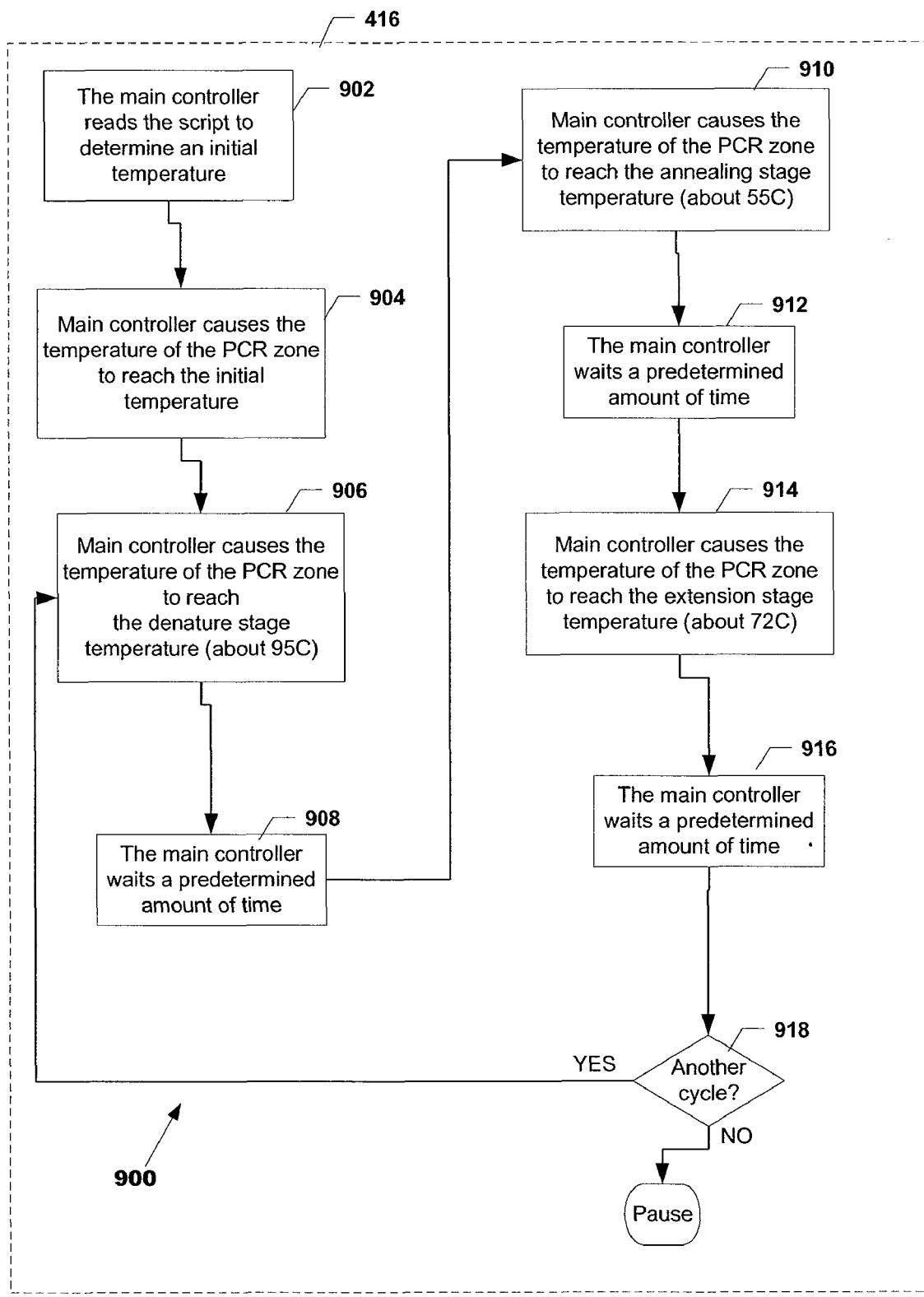
FIG. 9 is a flow chart illustrating a process according to some embodiments of the invention.

Referring now to FIG. 9, FIG. 9 is a flow chart illustrating a process 900, according to some embodiments, for implementing step 416 of process 400.

Process 900 may begin in step 902, where main controller 130 reads the script created by the user to determine an initial temperature for the PCR zone 131. In step 904, the main control causes the temperature of the PCR zone 131 to reach the initial temperature. For example, in step 904 main controller 130 may send a signal to the PCR zone temperature control system to go to the initial temperature.

In step 906, which may not be performed until after the PCR zone reaches the initial temperature, main controller 130 causes the temperature of the PCR zone 131 to reach the denature stage temperature (e.g., about 95° C.). In step 908, immediately after the temperature of the PCR zone 131 reaches the denature temperature, main controller 130 waits for a predetermined amount of time.

In step 910, after the predetermined amount of time has elapsed, main controller 130 causes the temperature of the PCR zone 131 to reach the annealing stage temperature (e.g., about 55° C.). In step 912, once the temperature of the PCR zone reaches the annealing temperature, main controller 130 waits for a predetermined amount of time.

In step 914, immediately after the predetermined amount of time has elapsed, main controller 130 causes the temperature of the PCR zone 131 reach the extension stage temperature (e.g., about 72° C.). In step 916, main controller 130 waits for a predetermined amount of time immediately after the temperature of the PCR zone reaches the extension stage temperature. After step 916 the process may proceed to step 918, where main controller 130 determines whether another PCR cycle is needed if another PCR cycle is needed, then process 900 may proceed back to step 906.

In some embodiments, step 906 includes turning on, or increasing the output of, source 251 while at the same time turning off, or decreasing the heat output of, TEC 202. Also, in some embodiments, step 908 includes turning off, or decreasing the output of, source 251 while at the same time controlling TEC 202 such that the annealing temperature is reached as quickly as possible.

Figure 10:
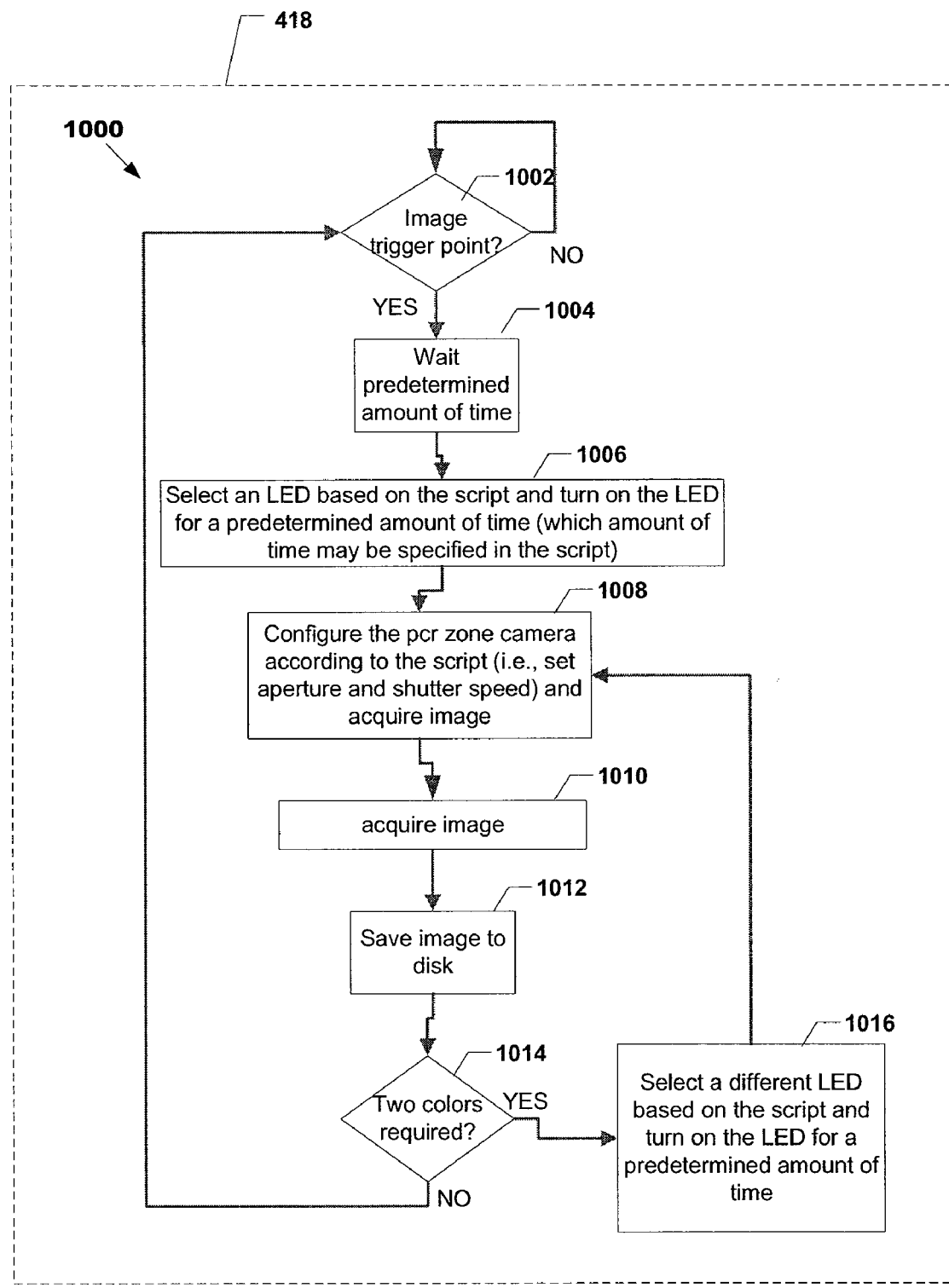
FIG. 10 is a flow chart illustrating a process according to some embodiments of the invention.

Referring now to FIG. 10, FIG. 10 is a flow chart illustrating a process 1000, according to some embodiments, for implementing step 418 of process 400.

Process 1000 may begin in step 1002, where a determination is made as to whether the image trigger point has been reached. In some embodiments the image trigger point is reached at the point in time when the PCR cycle begins the extension stage.

In step 1004, once the trigger point has been reached, main controller 130 may wait for a predetermined amount of time to allow the temperature to stabilize, which predetermined amount of time may have been specified in the script created by the user.

In step 1006, main controller 130 selects one of the LEDs 341 or 342 based on the script and turns on the selected LED for a predetermined amount of time, which amount of time may be specified in the script, and then immediately turns off the selected LED after the predetermined amount of time has expired.

In step 1008, controller 340 may configure the PCR zone 131 detector (e.g., detector 310) according to the script. For example, controller may set the detectors aperture and shutter speed.

In step 1010, detector 310 is used to acquire an image of the PCR zone 131. In step 1012 the image is saved. In step 1014, main controller 130 determines whether two colors are required. If two colors are required, then the process may proceed from step 1014 to step 1016, otherwise the process may proceed from step 1014 back to step 1002.

In step 1016, main controller 130 selects a different LED than the one selected in step 1006 and then turns on the selected LED for a predetermined amount of time and then immediately turns off the LED after the predetermined amount of time has expired. After step 1016, process 1000 may proceed to step 1008.

Figure 11:
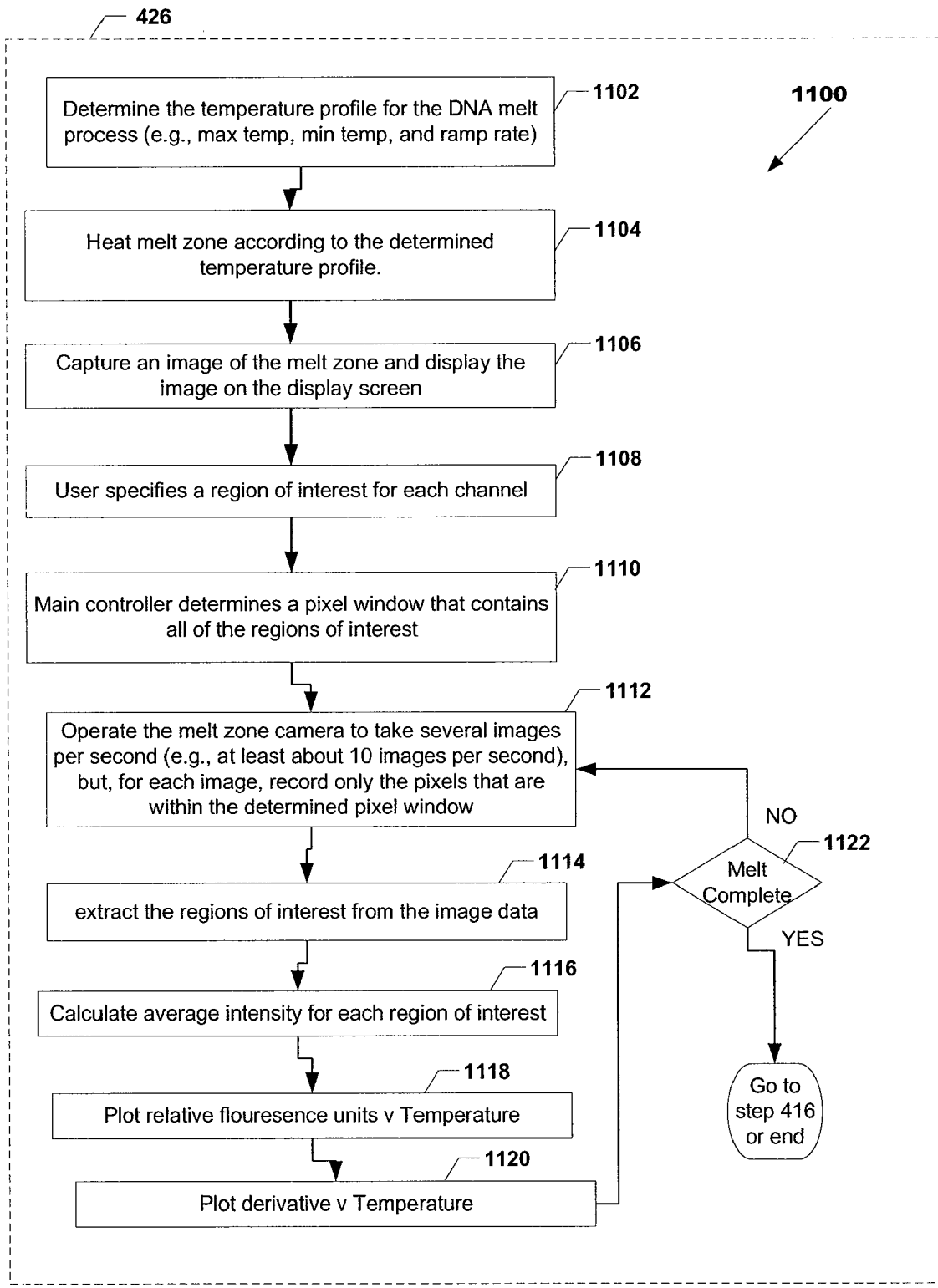
FIG. 11 is a flow chart illustrating a process according to some embodiments of the invention.

Referring now to FIG. 11, FIG. 11 is a flow chart illustrating a process 1100, according to some embodiments, for implementing step 426 of process 400.

Process 1100 may begin in step 1102, where the temperature profile for the melting process is determined. For example, the temperature profile may include a maximum temperature, a minimum temperature and a ramp rate. In step 1104, melting zone 132 is heated according to the determined temperature profile. For example, main controller 130 may cause the temperature control system 120 to cause the temperature of the melting zone 132 to reach the minimum temperature and, once the minimum temperature is reached, main controller 130 may cause the temperature control system 120 to increase the temperature of the melting zone to the maximum temperature at a rate equal to the ramp rate.

Figure 12:
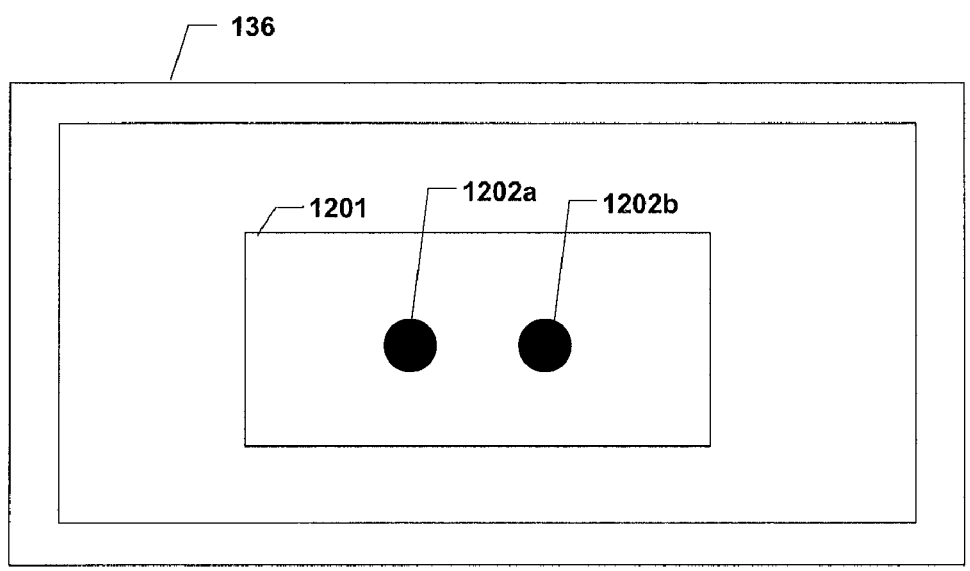
FIG. 12 illustrates an image of a DNA melting zone.

In step 1106, an image of the melting zone 132 is captured and displayed on the display device 136. FIG. 12 illustrates an image 1201 that may be displayed using display device 136 in step 1106. Each dot 1202 represents a channel 104 (i.e., dot 1202*a* represents channel 104*a* and dot 1202*b* represents channel 104*b*).

Figure 13:
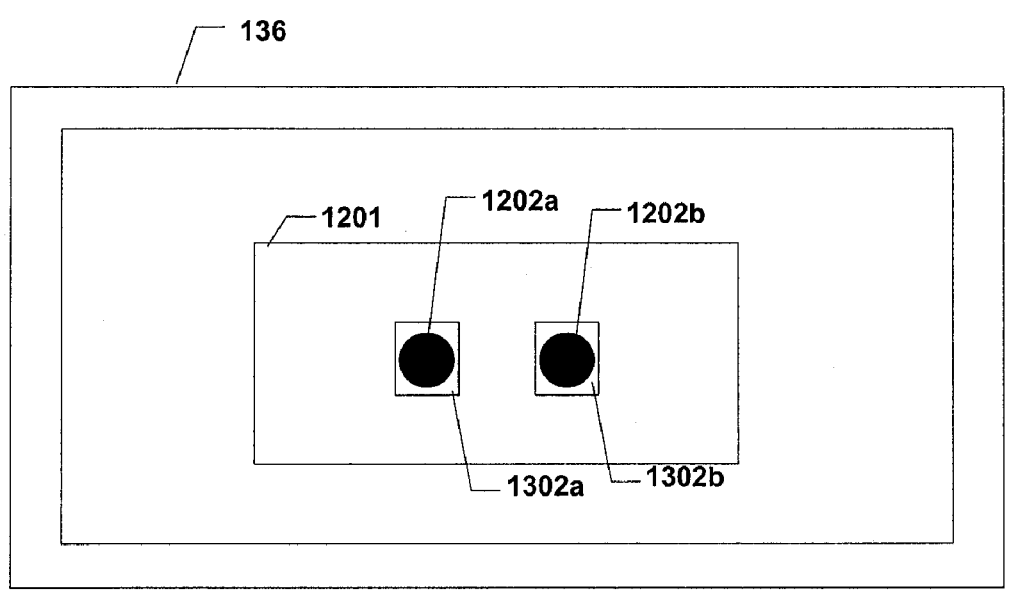
FIG. 13 illustrates a user defining regions of interest.

In step 1108, after the image is displayed, the user may specify a region of interest for each channel 104. This step is illustrated in FIG. 13, which shows a region of interest 1302 for each channel.

Figure 14:
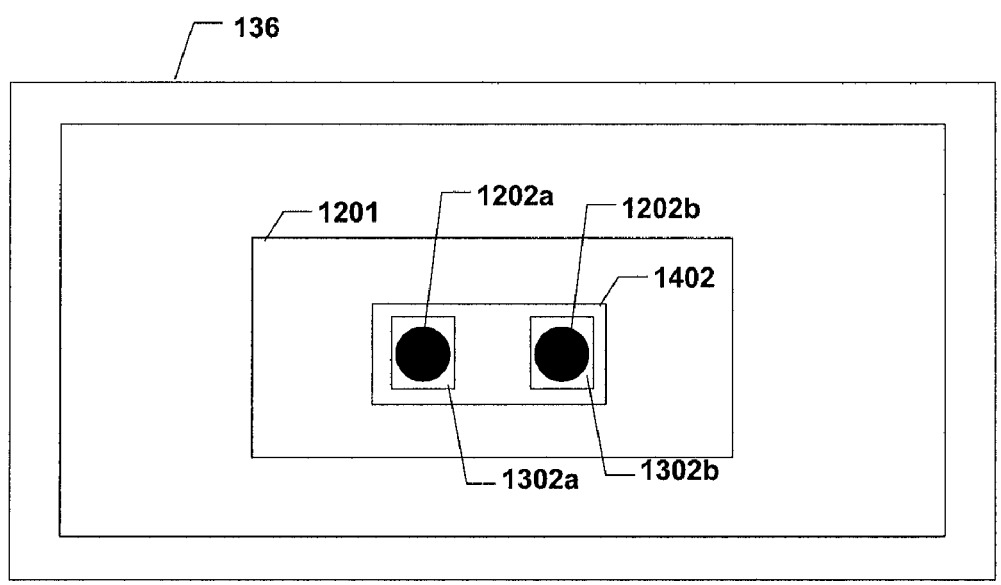
FIG. 14 illustrates a pixel window.

In step 1110, after the user specifies the regions of interest, main controller 130 may determine a pixel window 1402 (see FIG. 14) that contains all of the regions of interest. In some embodiments, the pixel window is the smallest rectangular pixel region of the sensor of detector 302 that includes all of the regions of interest.

In step 1112, the detector 302, which images melting zone 132, is operated so that it can take several images per second (e.g., at least about 10 images per second), but, for each image, record only the pixels that are included in the pixel window.

In step 1114, the regions of interest that were defined by the user are extracted from the recorded image data. In step 1116, the fluorescence intensity for each region of interest is calculated. In step 1118, main controller 130 plots relative fluorescence units vs. temperature. In step 1120, main controller 130 plots the derivative vs. temperature. In step 1122, a determination is made as to whether the melting process is complete. If the melting process is not complete the process may proceed back to step 1112, otherwise the process may proceed to step 416 of process 400.

While various embodiments/variations of the present invention have been described above, it should be understood that they have been presented by way of example only, and not limitation. Thus, the breadth and scope of the present invention should not be limited by any of the above-described exemplary embodiments.

Additionally, while the processes described above and illustrated in the drawings are shown as a sequence of steps, this was done solely for the sake of illustration. Accordingly, it is contemplated that some steps may be added, some steps may be omitted, and the order of the steps may be re-arranged.

What is claimed is:

1. A system for performing real-time PCR and melting of DNA, comprising:
    a microfluidic device comprising:
        a microfluidic channel having a PCR zone and a DNA melting zone, a first reagent well in fluid communication with the channel and a second reagent well in fluid communication with the channel;
        a sipper connected to the microfluidic device, the sipper being in fluid communication with the channel;
        a pump for forcing a sample to flow through the channel;
        a well plate comprising a buffer well for storing a buffer solution and a sample well for storing a sample solution containing a DNA sample;
        a buffer solution storage container for storing a buffer solution, the buffer solution storage container being in fluid communication with the buffer well of the well plate;
        a positioning system operable to position the well plate;
        a temperature control system for cycling the temperature of a sample while the sample is in the PCR zone of the channel and for providing heat for melting the DNA contained in the sample while the sample is in the DNA melting zone;
        an imaging system for detecting emissions from the PCR zone and from the DNA melting zone, the imaging system comprising: a first excitation source and a detector configured and arranged to detect emissions from the PCR zone and a second excitation source and a detector configured and arranged to detect emissions from the DNA melting zone;
        wherein the first excitation source for the PCR zone and the second excitation source for the DNA melting zone are different types; and
        a main controller in communication with (a) the temperature control system, (b) the positioning system, (c) the imaging system, and (d) a display device.

2. The system of claim 1, wherein the positioning system comprises a positioner.

3. The system of claim 2, wherein the positioning system further comprises a stepping drive operable to drive the positioner.

4. The system of claim 3, wherein the positioning system further comprises a controller for controlling the stepping drive.

5. The system of claim 1, wherein the imaging system comprises: a first light emitting diode directed to the PCR zone of the channel, a second light emitting diode directed to the PCR zone of the channel, and a laser directed to the melting zone of the channel.

6. The system of claim 5, wherein the first light emitting diode and the second light emitting diode are different colors, and wherein the first and second light emitting diodes are operated independently by the main controller.

7. The system of claim 1, wherein the second detector comprises a electron multiplying charge coupled device (EM-CCD).

8. The system of claim 1, wherein the imaging system further comprises a detector controller interfaced with the first detector and the second detector.

9. The system of claim 8, wherein the detector controller is communicatively connected to the main controller.

10. The system of claim 9, wherein the detector controller is connected to the main controller through an Ethernet hub.

11. The system of claim 1, wherein the temperature control system comprises a first heater configured to heat a sample within the PCR zone and a second heater configured to heat a sample within the DNA melting zone.

12. The system of claim 11, wherein the first heater comprises a first thermoelectric cooler (TEC) and the second heater comprises a second thermoelectric cooler (TEC).

13. The system of claim 12, wherein the temperature control system further comprises a first temperature controller coupled to the first TEC and a second temperature controller coupled to the second TEC.

14. The system of claim 13, wherein the first temperature controller is coupled to the main controller and the second temperature controller is coupled to the main controller.

15. The system of claim 14, wherein the first temperature controller consists of a power amplifier.

16. The system of claim 11, wherein the temperature control system further comprises a source of electromagnetic radiation, which source is arranged to illuminate the PCR zone.

17. The system of claim 11, wherein the first or second heater is configured to produce infrared radiation.

18. The system of claim 1, wherein the main controller monitors the sample during PCR amplification.

19. The system of claim 1, wherein the main controller monitors the sample during DNA melting.

20. The system of claim 1, wherein the main controller adjusts one or more of the imaging system, the temperature control system, the positioning system or the pump.

21. The system of claim 1, wherein the main controller triggers one or more additional PCR cycles in response to the data received from the imaging system.

22. The system of claim 1, wherein the main controller triggers one or more additional DNA melts in response to the data received from the imaging system.

23. The system of claim 1, wherein the main controller is configured to operate the first excitation source and the second excitation source independently, and wherein the main controller is configured to operate the second excitation source in response to analysis of the emissions detected by the PCR zone detector.

24. A system for performing real-time PCR and melting of DNA, comprising:
   a microfluidic device comprising: a microfluidic channel having a PCR zone and a DNA melting zone, a first reagent well in fluid communication with the channel and a second reagent well in fluid communication with the channel;
   a sipper connected to the microfluidic device, the sipper being in fluid communication with the channel;
   a pump for forcing a sample to flow through the channel;
   a well plate comprising a buffer well for storing a buffer solution and a sample well for storing a sample solution containing a DNA sample;
   a buffer solution storage container for storing a buffer solution, the buffer solution storage container being in fluid communication with the buffer well of the well plate;
   a positioning system operable to position the well plate;
   a temperature control system for cycling the temperature of a sample while the sample is in the PCR zone of the channel and for providing heat for melting the DNA contained in the sample while the sample is in the DNA melting zone;
   an imaging system for detecting emissions from the PCR zone and from the DNA melting zone, the imaging system comprising: a first excitation source comprising a laser emitting diode and a detector configured and arranged to detect emissions from the PCR zone and a second excitation source comprising a laser and a detector configured and arranged to detect emissions from the DNA melting zone;
   a main controller in communication with (a) the temperature control system, (b) the positioner, (c) the imaging system, and (d) a display device.

* * * * *